United States Patent
Hartley

(10) Patent No.: US 10,376,354 B2
(45) Date of Patent: Aug. 13, 2019

(54) SIDE BRANCH STENT GRAFT

(71) Applicant: Cook Medical Technologies LLC, Bloomington, IN (US)

(72) Inventor: David Ernest Hartley, Wannanup Western Australia (AU)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 14/843,544

(22) Filed: Sep. 2, 2015

(65) Prior Publication Data

US 2016/0089230 A1 Mar. 31, 2016

Related U.S. Application Data

(63) Continuation of application No. 11/231,621, filed on Sep. 21, 2005, now Pat. No. 9,149,355.

(Continued)

(51) Int. Cl.
*A61F 2/07* (2013.01)
*A61F 2/82* (2013.01)
(Continued)

(52) U.S. Cl.
CPC ............... *A61F 2/07* (2013.01); *A61F 2/844* (2013.01); *A61F 2/856* (2013.01); *A61F 2/89* (2013.01);
(Continued)

(58) Field of Classification Search
CPC ...... A61F 2002/065; A61F 2/07; A61F 2/856; A61F 2/852; A61F 2/954; A61F 2002/072
See application file for complete search history.

(56) References Cited

U.S. PATENT DOCUMENTS 5,122,154 A 6/1992 Rhodes
5,156,619 A 10/1992 Ehrenfeld
(Continued)

FOREIGN PATENT DOCUMENTS

AU 2005286843 3/2006
EP 0 709 066 5/1996
(Continued)

OTHER PUBLICATIONS

Japanese Patent Application No. 532614/2007, action dated Dec. 7, 2010, English translation provided.

(Continued)

*Primary Examiner* — Suba Ganesan
(74) *Attorney, Agent, or Firm* — Brinks Gilson & Lione

(57) ABSTRACT

A joining arrangement between a main tube (3) and a side arm (5) in a side arm stent graft (1). The side arm (5) is stitched into an aperture (11) in the main tube and is in fluid communication with it. The aperture is triangular, elliptical or rectangular and the side arm is cut off at an angle to leave an end portion having a circumferential length equal to the circumference of the aperture. The side arm can also include a connection socket (76) comprising a first resilient ring (79) around the arm at its end, a second resilient ring (80) spaced apart along the arm from the first ring and a zig zag resilient stent (82) between the first and second rings. The zig-zag resilient stent can be a compression stent. Both the main tube and the side arm are formed from seamless tubular biocompatible graft material.

11 Claims, 4 Drawing Sheets

Related U.S. Application Data

(60) Provisional application No. 60/611,774, filed on Sep. 21, 2004.

(51) Int. Cl.
*A61F 2/856* (2013.01)
*A61F 2/89* (2013.01)
*A61F 2/844* (2013.01)
*A61F 2/954* (2013.01)
*A61F 2/06* (2013.01)

(52) U.S. Cl.
CPC ......... *A61F 2/954* (2013.01); *A61F 2002/061* (2013.01); *A61F 2002/065* (2013.01); *A61F 2002/067* (2013.01); *A61F 2002/072* (2013.01); *A61F 2002/075* (2013.01); *A61F 2002/821* (2013.01); *A61F 2002/828* (2013.01); *A61F 2220/0075* (2013.01); *A61F 2230/0008* (2013.01); *A61F 2230/0019* (2013.01); *A61F 2230/0023* (2013.01)

(56) References Cited

U.S. PATENT DOCUMENTS

| | | | |
|---|---|---|---|
| 5,443,497 A | 8/1995 | Venbrux | |
| 5,591,228 A | 1/1997 | Edoga | |
| 5,639,278 A | 6/1997 | Dereume et al. | |
| 5,643,340 A | 7/1997 | Nunokawa | |
| 6,017,363 A | 1/2000 | Hojeibane | |
| 6,019,788 A | 2/2000 | Butters et al. | |
| 6,033,435 A * | 3/2000 | Penn | A61F 2/856 623/1.15 |
| 6,090,133 A | 7/2000 | Richter et al. | |
| 6,165,195 A | 12/2000 | Wilson et al. | |
| 6,197,049 B1 | 3/2001 | Shaolian et al. | |
| 6,749,628 B1 | 6/2004 | Callol et al. | |
| 7,141,060 B1 | 11/2006 | Metz et al. | |
| 2002/0193864 A1 | 12/2002 | Khosravi et al. | |
| 2003/0088306 A1 | 5/2003 | Rakos et al. | |
| 2003/0176911 A1 * | 9/2003 | Iancea | A61F 2/07 623/1.13 |
| 2003/0199967 A1 | 10/2003 | Hartley et al. | |
| 2004/0193254 A1 * | 9/2004 | Greenberg | A61F 2/07 623/1.35 |

FOREIGN PATENT DOCUMENTS

| | | |
|---|---|---|
| EP | 0 959 811 | 7/2004 |
| JP | 8-117259 | 5/1996 |
| JP | 2001/501496 | 2/2001 |
| WO | 97/41803 | 11/1997 |
| WO | 01/52769 | 7/2001 |
| WO | 2004/064686 | 8/2004 |
| WO | 2004/089249 | 10/2004 |

OTHER PUBLICATIONS

Japanese Patent Application No. 532614/2007, action dated Oct. 4, 2011, English translation provided.
CA Patent Application No. 2580822, action dated Mar. 1, 2012.
EP Patent Application No. 05798684.6, Communication dated Aug. 29, 2012.
EP Patent Application No. 05798684.6, Communication dated Feb. 26, 2010.
EP Patent Application No. 05798684.6, Communication dated Mar. 24, 2015.
International Search Report, PCT/US2005/033676, filed Sep. 21, 2005, search completed Jan. 31, 2006.
International Preliminary Report on Patentability, PCT/US2005/033676, filed Sep. 21, 2005, report completed Mar. 12, 2007.

* cited by examiner

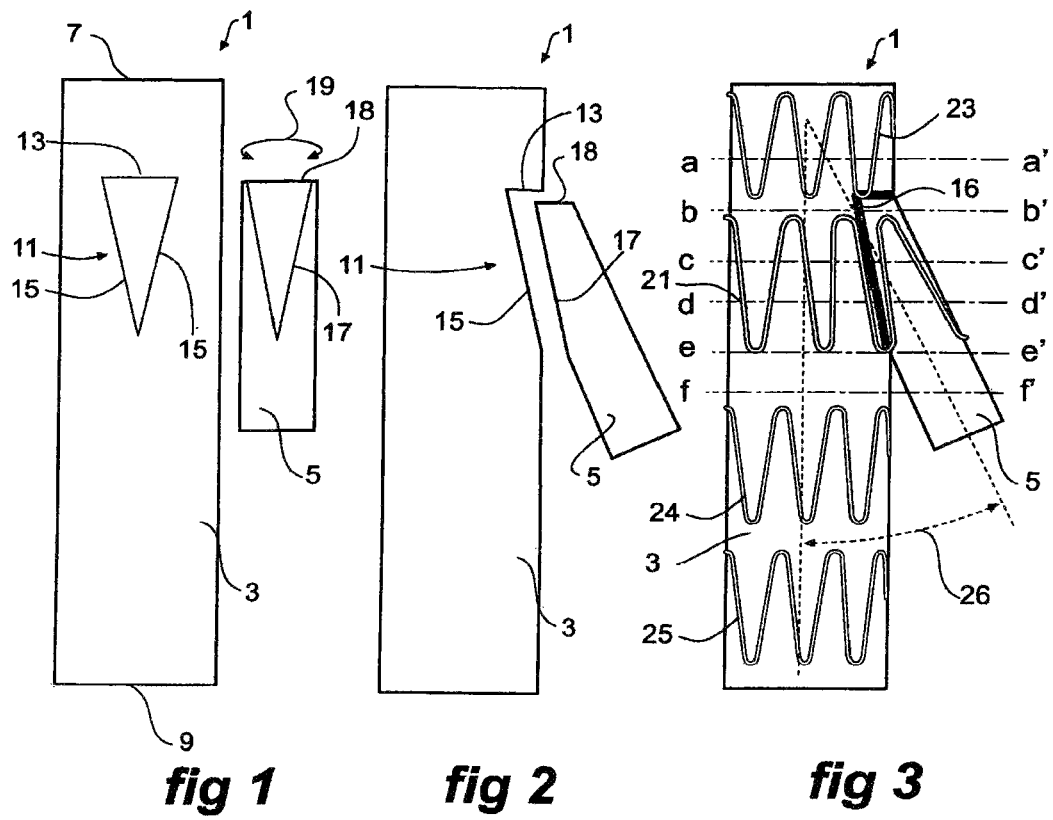
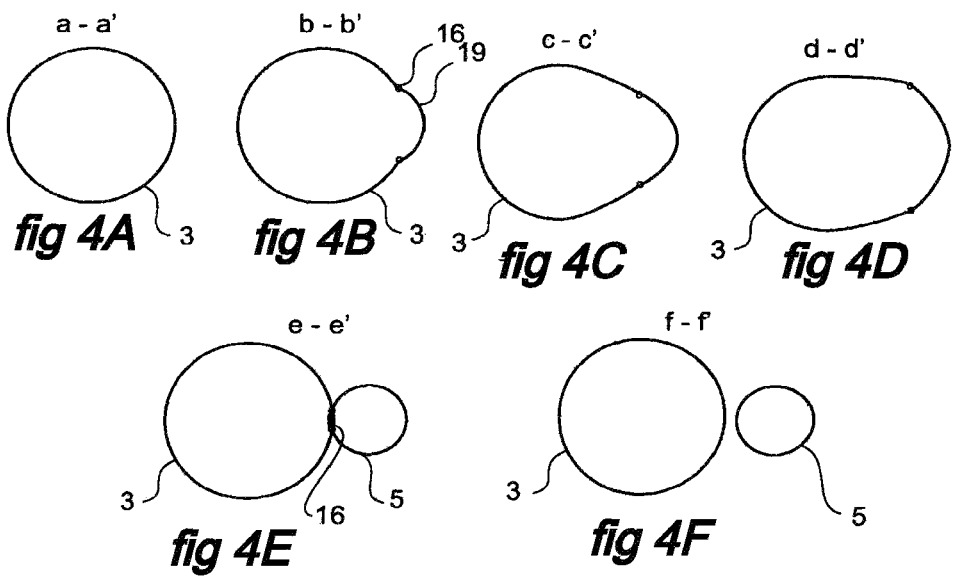

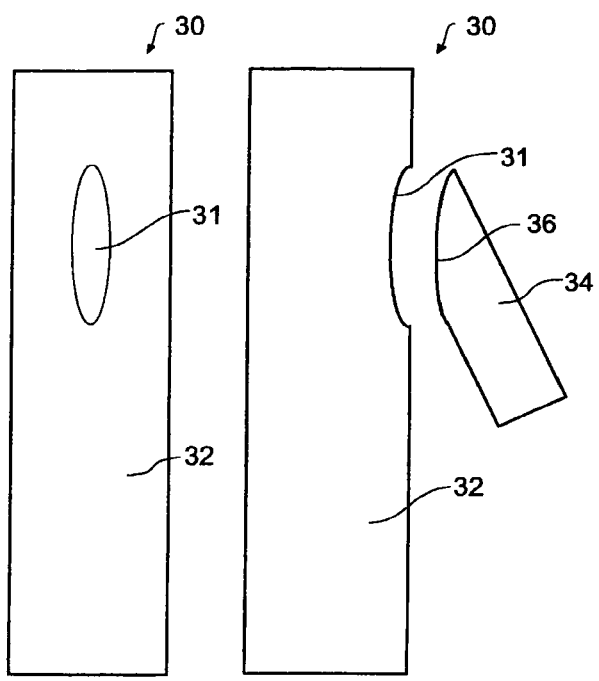
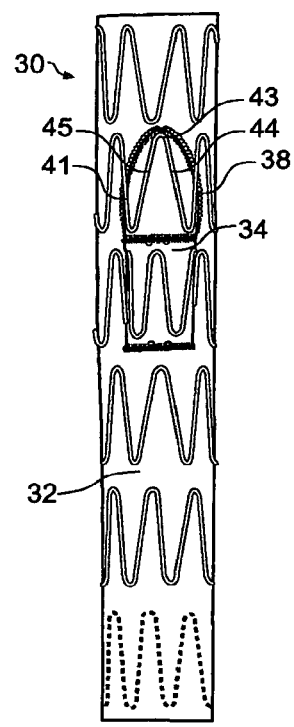
fig 5  fig 6  fig 8
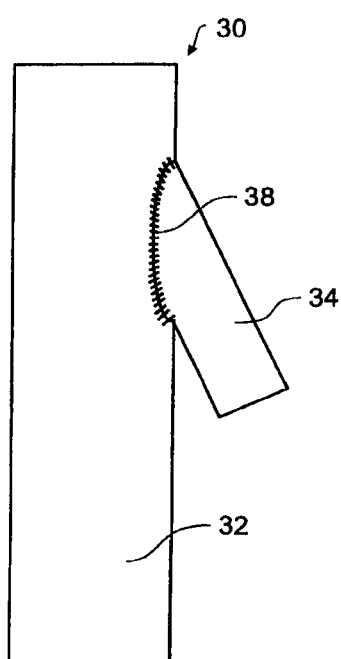
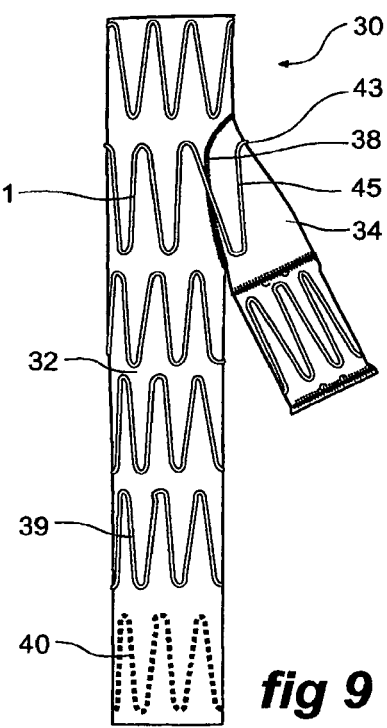
fig 7  fig 9

SIDE BRANCH STENT GRAFT

CROSS-REFERENCE TO RELATED APPLICATIONS

This continuation application claims priority of U.S. Utility patent application Ser. No. 11/231,621, filed Sep. 21, 2005, which claims priority to provisional application Ser. No. 60/611,774, filed Sep. 21, 2004, the entirety of each of which are hereby incorporated by reference.

TECHNICAL FIELD

This invention relates to a stent graft used to restore the patency of a body lumen and in particular relates to a side branch or side arm stent graft.

BACKGROUND OF THE INVENTION

Where damage has occurred to an internal vessel of the human or animal body such as a blood vessel either by disease or by trauma it is possible to introduce to the blood vessel a stent graft by endoluminal techniques which will restore patency of the blood vessel across the damaged region. Often such damaged regions include side branch vessels. To ensure the blood flow can go into the side branch vessel side branch stent grafts are used.

There can be a problem with such side branch stent grafts that in the region of the bifurcation or exit of a side branch from a main tube, disruption to blood flow can occur. This may result in thrombosis occurring which could at least partially block the stent graft. Also, without suitable geometry, blood flowing through such regions may not adequately flow into the side arm or side branch.

It is the object of this invention to provide a branched or side arm stent graft which does not compromise blood flow in the main lumen of the stent graft and allows blood flow into the side arm.

Throughout this specification the term distal with respect to a portion of the vasculature, a deployment device or a stent graft is the end of the vasculature, deployment device or stent graft further away in the direction of blood flow away from the heart and the term proximal means the portion of the vasculature, deployment device or end of the stent graft nearer to the heart. When applied to other vessels similar terms such as caudal and cranial should be understood.

SUMMARY OF THE INVENTION

In one form therefore the invention is said to reside in a side arm stent graft comprising a main tube of a biocompatible material and a side arm tube of a biocompatible material extending from the main tube at an acute angle thereto and being stitched thereto and in fluid communication therewith, wherein the stent graft further comprises a triangular aperture in the main tube around the periphery of which the side arm tube is stitched, the triangular aperture having a base and a pair of sides, and an end of the side arm tube having a bevel to leave an end portion having a circumferential length equal to the length of the base of the triangular aperture and a length of the bevel equal to the length of the side of the triangular aperture, whereby the side arm tube is stitched to the main tube around the periphery of the triangular aperture with the end portion abutting the base of the triangular aperture and the bevel abutting the sides of the triangular aperture.

In an alternative form the invention is said to reside in a side arm stent graft comprising a main tube of a biocompatible material and a side arm tube of a biocompatible material extending from the main tube at an acute angle thereto and being stitched thereto and in fluid communication therewith, wherein the stent graft further comprises an elongated aperture in the main tube around the periphery of which the side arm tube is stitched, the elongate aperture having a circumferential length, and an end of the side arm tube having a bevel to leave an end portion having a circumferential length equal to the circumferential length of the elongate aperture, whereby the side arm tube is stitched to the main tube around the periphery of the elongate aperture.

In an alternative form the invention comprises a side arm stent graft comprising a main tube of a biocompatible material and a side arm tube of a biocompatible material extending from the main tube and being stitched thereto and in fluid communication therewith, wherein the stent graft further comprises an elongate aperture in the main tube and an angled inner end on the side arm tube, the periphery of the inner end of the side arm tube being stitched to the periphery of the aperture, whereby the circumference of the joined region of the main tube and side arm tube increases along the length of the stitching at a first end of the joined region, to the sum of the circumferences of the main tube and the side arm tube at the other end of the joined region.

In one embodiment the elongate aperture is substantially rectangular.

In an alternative embodiment the elongate aperture is substantially elliptical.

In a further embodiment the elongate aperture is substantially triangular.

The acute angle may be in the range of from 15 to 60 degrees and preferably 15 to 45 degrees.

In a further form the invention is said to reside in a side arm stent graft comprising a main tube of a biocompatible material, a fenestration in the main tube defined by a peripheral edge to the fenestration and a side arm tube of a biocompatible material being joined around the peripheral edge at a join region by stitching and extending from the main tube at an acute angle thereto and in fluid communication with the main tube, whereby the circumference of the join region of the main tube and side arm tube increases along the length of the stitching at a first end of the joined region from the circumference of the main tube to the sum of the circumferences of the main tube and the side arm tube at the other end of the join region.

Preferably the fenestration can be selected from an elongate aperture, a substantially rectangular aperture or a substantially elliptical aperture. Alternatively the fenestration may be substantially triangular.

It will be seen that by this invention there is provided a main flow lumen whose circumference increases from that of the main flow tube or stent graft to that of the sum of the main flow tube plus the side arm tube before the actual side arm tube flow branches off. By this arrangement the flow of blood through the replacement vessel is enabled to flow both through the main branch and into the side arm without significant interruption.

Biocompatible graft material such as dacron is available in tubular form and hence it is relatively straight forward to cut the aperture in a length of the tubular material of a first diameter and to cut a bevel in the end of a piece of tube of another diameter and to join then according to the present invention.

The side arm stent graft preferably further comprises a plurality of self expanding stents along the main tube, one of the self expanding stents extending around both the main body and the side arm. Preferably the self expanding stent extending around both the main body and the side arm comprises a bend adjacent to the proximal end of the stitching and the struts extending down either side of the side arm.

In a further form the invention is said to reside in a method of assembling a side arm stent graft comprising the steps of:
    forming a triangular aperture in a main tube, the triangular aperture being defined by a base and a pair of sides;
    forming a bevel cut out on a side arm tube to define a remaining end piece and beveled edges;
    stitching the beveled edges to the sides of the triangular aperture; and
    stitching the remaining end piece of the side arm tube to the base of the triangular aperture.

Preferably the method further includes the step of turning inside out the side arm and inserting it into the main tube such that the remaining straight end at the bevelled end piece of the side arm is aligned with the base of the triangular aperture and the bevelled edges are aligned with the sides of the triangular aperture before the stitching steps.

Preferably both the main tube and the side arm tube are formed from a seamless tube of a biocompatible graft material.

BRIEF DESCRIPTION OF THE DRAWING

This then generally describes the invention but to assist with understanding reference will now be made to the accompanying drawings which show various embodiments of the invention.

In the drawings:

FIG. 1 shows schematically a main tube and a side branch for a stent graft;

FIG. 2 shows a side view of the embodiment shown in FIG. 1;

FIG. 3 shows a view of the embodiment shown in FIGS. 1 and 2 with the side arm stitched into the main tube;

FIGS. 4A to F show the circumferences of the main tube and side arm at various positions along the joining region of the main tube and side arm tube.

FIGS. 5, 6 and 7 show an alternative form of connection of a side arm to a main tube according to the present invention;

FIG. 8 shows a front elevation of a side branch stent graft made according to the connection arrangement shown in FIGS. 5, 6 and 7;

FIG. 9 shows a side elevation of a side branch stent graft made according to the connection arrangement shown in FIGS. 5, 6 and 7;

DETAILED DESCRIPTION

Figures 10, 11:
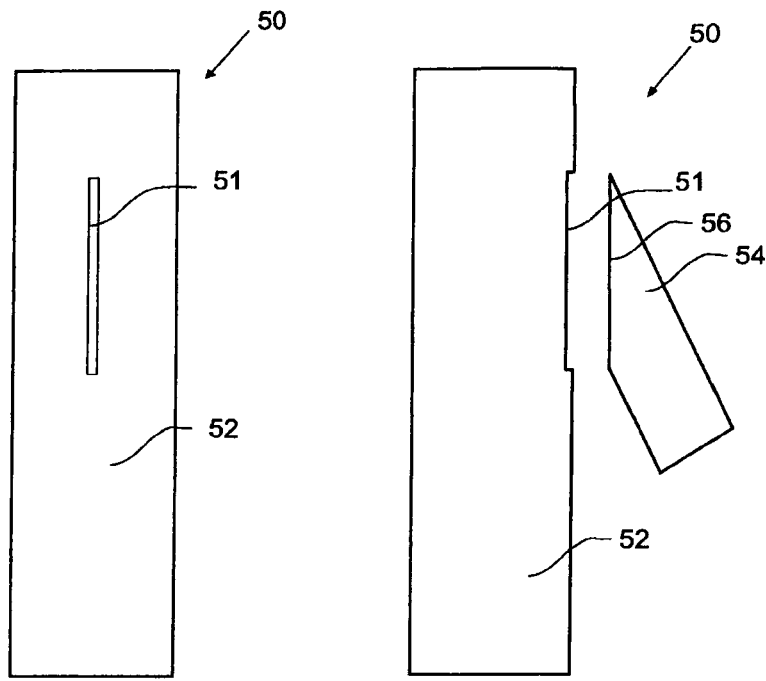
FIGS. 10, 11 and 12 show a still further arrangement of joining of a side arm tube to a main tube.

Now looking at the drawings and more particularly the first embodiment shown in FIGS. 1 to 4 it will be seen that the stent graft 1, according to one embodiment of the present invention, comprises a biocompatible graft material main tube 3 and a side arm 5 also comprises a biocompatible graft material.

For the purpose of assisting in the explanation of the present invention the stent graft main tube 3 has a proximal end 7 and a distal end 9 and blood flow would normally be from the proximal end 7 to the distal end 9.

To join the branch tube 5 to the main tube 3, according to one embodiment of the invention, a triangular aperture or fenestration generally shown as 11 is cut into the main tube 3. The triangular aperture or fenestration 11 is in the shape of an isosceles triangle with the base 13 at the proximal end and the substantially equal length sides 15 more distal. The side arm 5 has a bevel cut in it at one of its ends such that the remainder 18 of the circumference of the side arm after the bevel 17 is cut into the side arm has a semi-circumference 19 which is substantially equal to the length of the base 13 of the triangular aperture or fenestration 11. The length of the bevel 17 is substantially equal to the length of the sides 15 of the triangular aperture or fenestration 11.

FIG. 2 shows a side view with the side arm 5 offered up to the aperture 11 in the main tube 3.

FIG. 3 shows the side arm 5 stitched into the main tube 3 and it will be noted that the stitching 16 extends along the base 13 of the triangular aperture or fenestration 11 on the main tube and then along the sides 15 of the isosceles triangle.

FIG. 3 shows the positions of cross-sections a-a', b-b', c-c', d-d', e-e' and f-f' and these cross sections are shown in FIGS. 4A to F.

FIG. 4A shows the circumference of the main tube 3. FIG. 4B shows the main tube 3 plus the region 19 of the side arm 5 stitched on.

Through FIGS. 4C and D the diameter of the added portion increases until in FIG. 4D the circumference of the tube is substantially equal to the total of the circumferences of both the main tube 3 and side tube 5. At 4E the side tube commences to branch off and at 4F the side tube 5 has completely branched off from the main tube 3. By this arrangement the cross sectional area of the lumen of the stent graft increases to essentially that of the sum of the main tube and side arm before the side arm branches off and by this arrangement there is not significant obstruction to blood flow and blood is able to flow into the side arm easily.

In practice a self-expanding stent 21 is placed on the outside of the stent graft at the branch or join region to assist with maintaining the side arm and main tube in a more circular cross section and as open as possible as shown in FIGS. 3 and 4D.

FIG. 3 also shows other self-expanding stents on the main body of the stent graft. These include a proximal stent 23 and more distal stents 24 and 25. The actual number of stents would depend upon the length of the main tube proximally and distally of the region of the join of the side arm. In the case of a stent graft to be deployed into the common iliac artery with the side arm adapted to extend towards the internal iliac artery normally there would only be a short length of main tube and a single stent proximal of the join to the side arm.

In this embodiment the side arm extends from the main tube 3 at an angle designated by the numeral 26. This angle may be in the region of from 15 to 45 degrees.

In one particular embodiment the main tube 3 may have a diameter of 12 mm and hence a circumference of 38 mm. The side tube may have a diameter of 8 mm and hence a circumference of 26 mm. The base of the triangular aperture or fenestration 11 may have a length of 13 mm and the sides of the triangular aperture or fenestration 11 may have a length of 20 mm. Hence the side arm 5 has a bevel cut into it leaving a semi circumference 19 of 13 mm and a length of the bevel 17 of 20 mm. The stent graft may have an overall length of 103 mm. In the case of a stent graft to be deployed into the common iliac artery with the side arm adapted to extend towards the internal iliac artery normally there may be a length of main tube of 16 mm proximal of the join to the side arm and up to 68 mm distal of the join to the side arm. The side arm may have a diameter of 8 mm and a length distally of the join region of up to 25 mm. It will be realised that for stent grafts to be deployed into the ascending or descending aorta with side arms to extend into their respective branch vessels, other lengths and diameters will be applicable.

One method by which the side arm stent graft according to the present invention may be assembled by stitching is as follows:

The triangular aperture is cut out of the main tube and the bevel cut out of the side arm.

The side arm is turned inside out and inserted into the main tube such that the remaining straight end at the bevelled end of the side arm is aligned with the base of the triangular aperture and the bevelled edges are aligned with the sides of the triangular aperture.

The two tubes are temporarily tacked together.

The bevelled edges are stitched to the sides of the triangular aperture.

The bevelled end of the side arm is stitched to the base of the triangular aperture.

The side arm is then pulled out through the aperture.

The necessary stents are then stitched to the main tube and the side arm.

Both the side arm 5 and the main tube 3 are formed from a seamless tube of a biocompatible graft material. This means that when the stent graft is compressed into an endovascular delivery device seams along the length of the tube do not compromise the size of the stent graft.

FIGS. 5, 6, 7, 8 and 9 show an alternative embodiment of branch stent graft according to the present invention.

In this embodiment the stent graft 30 has an elongate elliptical fenestration or aperture 31 which is cut in the main body 32 and a side arm 34 has a angled and curved cut end 36 such that the circumference of the elliptical fenestration 31 is substantially the same length as the circumference of the angled and curved end 36.

FIG. 7 shows the side arm 34 stitched into the main body 32 with stitching 38.

FIG. 8 shows a front elevation and FIG. 9 shows a side elevation of a side branch stent graft made according to the connection arrangement shown in FIGS. 5, 6 and 7. After the side arm 34 has been sewn into the main tubular body 32 by stitching 38 around the periphery of the aperture 31 (FIG. 5) and the circumference of the angled and curved end 36 (FIG. 6), self expanding zig-zag Z stents 39 are sewn onto the outside of the tubular body 32 except for the distal-most stent 40 which is mounted internally. It will be noted that the stent 41, in the position in which the side arm extends from the main tubular body, extends around both the main tubular body 32 and the side arm 34.

In particular it can be noted that the stent 41 has a bend 43 between struts 44 and 45 adjacent to the proximal end of the stitching 38 and that the struts 44 and 45 extend on either side of the side arm 34.

By this arrangement the circumference of the main body and side arm increases from being the circumference of the main body at the proximal end of the join region until at the distal end of the join region, the total circumference is the circumference of the main body plus the circumference of the side arm and it is after this that the side arm actually exits.

Figure 12:
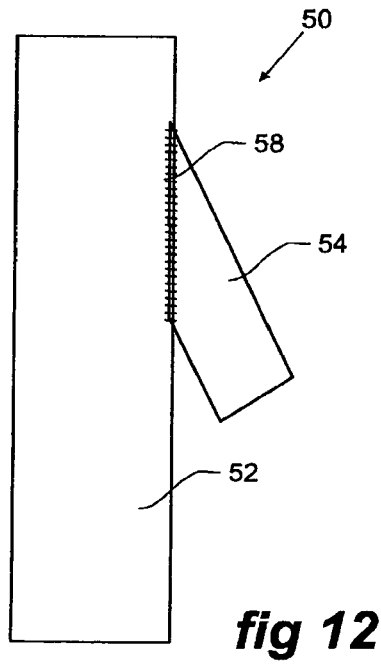

FIGS. 10, 11 and 12 show a further embodiment of the present invention. In this embodiment the stent graft 40 has an elongate substantially rectangular slot 51 formed in the main tube 52 and a side arm 54 has a bevelled or angled end 56 which is stitched into the main body as shown in FIG. 12 using stitching 58. The bevelled end 56 has a circumference which is substantially the same length as the length of the periphery of the aperture 51.

Figure 13:
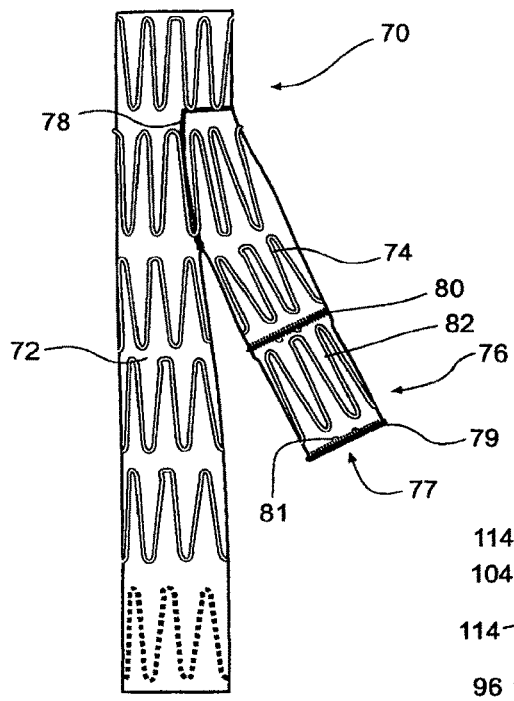
FIG. 13 shows a side branch stent graft or prosthesis of the type adapted for deployment into the iliac arteries and including one embodiment of the present invention.

FIG. 13 shows a side branch stent graft or prosthesis of the type adapted for deployment into the iliac arteries, for instance, such that a bridging stent can extend from the side arm into the internal iliac or hypogastric artery.

The stent graft 70 has a main tubular body 72 and a side arm 74. Both the main tubular body and the side arm are formed from a seamless tube of a biocompatible graft material such as Dacron. A triangular aperture is formed in the main tube and a bevel cut into the inner end of the side arm and the side arm stitched into the triangular aperture with stitching 78 according to the method of the present invention. The side arm has a connection socket arrangement 76 at its distal end 77. The connection socket arrangement 76 comprises a first resilient ring 79 stitched to its terminal or distal end 77 and a second resilient ring 80 spaced apart from the first ring 79. Each ring 79 and 80 is formed from at least two turns and preferably three turns of nitinol wire and the ends of the nitinol wire terminate in loops 81. The use of the loops 81 prevents sharp ends from the nitinol wire from digging into the vasculature into which the stent graft is deployed. Between the first ring 79 and the second ring 80 is a stent 82 formed from a resilient material. The resilient stent 82 is formed from nitinol wire, for instance, and is made to be of a size which is at rest slightly smaller than the diameter of the side arm 74 and hence when sewn on to the outside of the side arm 74 it provides a diameter reducing effect on the side arm 74.

When a bridging stent such as a balloon expandable stent is placed into the socket 76 and expanded, the rings 79 and 80 provide firm locking for the balloon expanded stent and the resilient stent 82, which is expanded by the balloon expanded stent while it is being balloon expanded, provides a compressive effect to keep tension on the balloon expanded stent. By this means a firm connection can be obtained between the side arm and a bridging stent. A similar gripping effect can be obtained with the use of a bridging stent in the form of a self-expanding stent, a composite stent or other form of leg extension.

Figure 14:
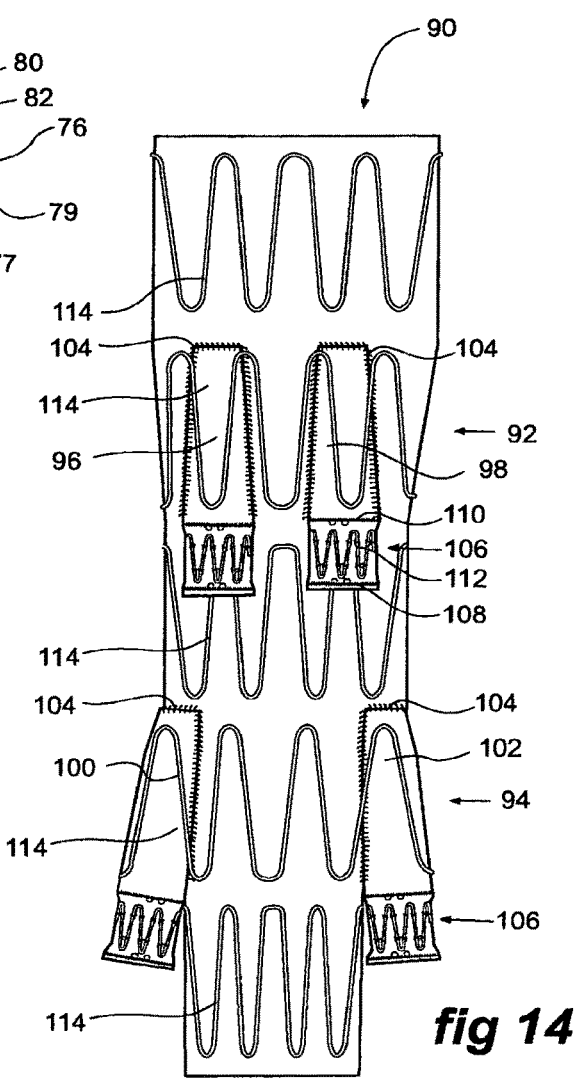
FIG. 14 shows an alternative form of stent graft having side branches connected to a main tube according to one embodiment of the present invention.

FIG. 14 shows an alternative form of stent graft having a number of side branches according to the present invention. This form of stent graft is adapted for deployment into the mid-aorta region where major vessels branch off the aorta. In this embodiment the stent graft 90 has a pair of tapered regions 92 and 94. At the taper 92 a pair of side branches 96 and 98 branch off and at the taper 94 a further pair of side branches 100 and 102 branch off the main tube. The side branch 96 is intended for connection to the superior mesenteric artery, the side branch 98 is intended for connection to the coeliac artery, the side branch 100 is intended for connection to a renal artery and the side branch 102 is intended for connection to the other renal artery. Each of the four side branches 96, 98, 100 and 102 are joined to the main tube by an arrangement similar to that shown in FIGS. 1 to 3. In each case, however, as the main tube is tapered the side branches extend at substantially the same angle as the main tube.

In the case of each side arm a triangular aperture is formed in the main tube and a bevel cut into the inner end of the side arm and the side arm stitched into the triangular aperture with stitching 104 according to the method of the present invention. Each side arm has a connection socket arrangement 106 at its distal end. The connection socket arrangement 106 comprises a first ring 108 stitched to its terminal or distal end and a second ring 110 spaced apart from the first ring 108. Each ring 108 and 110 is formed from at least two turns and preferably three turns of nitinol wire and the ends of the nitinol wire terminate in loops. The use of the loops prevents sharp ends from the nitinol wire from digging into the vasculature into which the stent graft is deployed. Between the first ring 108 and the second ring 110 is a stent 112 formed from a resilient material. The resilient stent 112 is formed from nitinol wire, for instance, and is made to be of a size which is at rest slightly smaller than the diameter of the side arm 98 and hence when sewn on to the outside of the side arm 98 it provides a diameter reducing effect on the side arm 98.

The main stent graft has a series of self expanding stents 114 along its lengths and it will be particularly noted that self expanding stents extend over the junction regions of the side arms to assist with holding the side arms open to blood flow.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A side arm stent graft comprising a main tube of a biocompatible material and a side arm tube comprising a of biocompatible material extending from the main tube at an angle thereto and attached thereto at a joined region by stitching, the joined region having a first end and a second end, and being in fluid communication therewith, wherein the side arm stent graft further comprises a triangular aperture in the main tube around the periphery of which the side arm tube is attached, the triangular aperture having a base at a proximal end and a pair of sides distal to the base, and an end of the side arm tube having a bevel to leave an end portion having a circumferential length equal to the length of the base of the triangular aperture and a length of the bevel equal to the length of the sides of the triangular aperture, whereby the side arm tube is stitched to the main tube around the periphery of the triangular aperture with the end portion abutting the base of the triangular aperture and the bevel abutting the sides of the triangular aperture, further comprising a plurality of self-expanding stents along the main tube, wherein a self-expanding stent of the plurality of self-expanding stents extends around both the main tube and the side arm tube at the joined region, wherein a circumference of the joined region of the main tube and side arm tube increases along the length of the stitches at the first end of the joined region from a circumference of the main tube to the sum of the circumferences of the main tube and the side arm tube at the second end of the joined region.

2. A side arm stent graft as in claim 1 wherein the side arm tube extends from the main tube at an acute angle thereto, the acute angle being in the range of from 15 to 45 degrees.

3. A side arm stent graft as in claim 1 wherein the self expanding stent extending around both the main tube and the side arm tube comprises a bend adjacent to a proximal end of the stitching and struts extending down either side of the side arm tube.

4. A side arm stent graft as in claim 1 wherein the side arm tube extends from the main tube at an acute angle thereto, the acute angle being in range of from 15 to 60 degrees.

5. The side arm stent graft of claim 1, wherein the triangular aperture has the shape of an isosceles triangle.

6. The side arm stent graft of claim 1, wherein the stitching extends along the base of the triangular aperture on the main tube and along the sides triangular aperture.

7. The side arm stent graft of claim 1, wherein the self-expanding stent extending around both the main tube and the side arm tube is positioned outside of the main tube and the side arm tube.

8. The side arm stent graft of claim 1, wherein the self-expanding stent extending around both the main tube and the side arm tube is positioned at the joined region.

9. The side arm stent graft of claim 1, wherein the self-expanding stent extending around both the main tube and the side arm tube comprises a plurality of struts and proximal and distal bends between adjacent struts.

10. The side arm stent graft of claim 1, further comprising a connection socket arrangement positioned on an end of the side arm tube, the connection socket arrangement comprising a first resilient ring and a second resilient ring spaced apart from the first ring.

11. The side arm stent graft of claim 10, wherein a stent is positioned between the first ring and the second ring of the connection socket arrangement.

* * * * *